US005078746A

United States Patent [19]

Garner

[11] Patent Number: 5,078,746
[45] Date of Patent: Jan. 7, 1992

[54] FEMORAL STEM DISTAL CENTRALIZER

[75] Inventor: Steven A. Garner, Memphis, Tenn.

[73] Assignee: Richards Medical Company, Memphis, Tenn.

[21] Appl. No.: 301,939

[22] Filed: Jan. 25, 1989

[51] Int. Cl.[5] ............................................. A61F 2/28
[52] U.S. Cl. ........................................ 623/16; 606/95
[58] Field of Search ..................... 623/16, 18, 20, 22, 623/23; 128/92 R, 92 YZ, 92 YK, 92 VP, 92 VQ

[56] References Cited

U.S. PATENT DOCUMENTS

| 3,906,550 | 9/1975 | Rostoker et al. | 623/23 X |
| 4,080,666 | 3/1978 | Fixel | 623/23 X |
| 4,302,855 | 12/1981 | Swanson | 623/16 A |
| 4,670,015 | 6/1987 | Freeman | 623/23 |
| 4,705,032 | 11/1987 | Keller | 623/23 X |

FOREIGN PATENT DOCUMENTS

| 0243298 | 10/1987 | European Pat. Off. | 623/23 |
| 3304476 | 9/1983 | Fed. Rep. of Germany | 623/22 |
| 8400332 | 4/1986 | World Int. Prop. O. | 623/22 |

Primary Examiner—David J. Isabella
Attorney, Agent, or Firm—Kirkpatrick & Lockhart

[57] ABSTRACT

A device for centralizing a prosthetic femoral stem within a prepared natural femur and plugging the femoral canal inculdes a first member having a shape generally similar to the shape of the femoral stem for temporary insertion within the natural femur, a rod member for slidable insertion through a bore in the first member, and a second member releasably connected to the distal end of the rod member for permanent insertion within the natural femur for aligning the distal end of the femoral stem and plugging the canal of the natural femur.

9 Claims, 2 Drawing Sheets

FEMORAL STEM DISTAL CENTRALIZER

BACKGROUND OF THE INVENTION

1. Field of the Invention

The present invention relates to orthopedic devices and, more particularly, to a device for centralizing a prosthetic femoral stem.

2. Description of the Prior Art

In some arthritic patients, or those having other degenerative joint diseases, treatment may involve replacing the affected joint with a prosthesis. A prosthetic femoral stem with an integral or modular head, for example, can be used to replace the natural femoral head and neck. The surgeon removes the diseased femoral head and neck, and reams the bone to shape the canal within the femur to accept the stem of the prosthesis. The prosthetic femoral stem is placed in the canal where it is surrounded by bone cement. A problem often experienced with insertion of the femoral stem, however is centering it correctly and maintaining it in the desired position until the cement sets. Simply placing the prosthesis in the canal and surrounding it with bone cement does not assure that the prosthesis will be in the desired position or that the cement will be applied uniformly.

There is a need for a device for centralizing the prosthetic femoral stem along with plugging the femoral canal to prevent cement from moving distally. There is a further need for such a device which can be easily used with existing prostheses and surgical techniques.

SUMMARY OF THE INVENTION

The present invention provides a device for centralizing and plugging a prosthetic femoral stem which has a proximal end and a distal end. The device includes a first member, preferably having a shape generally similar to the shape of the femoral stem, for temporary insertion within the natural femur. The first member has means for assuring that the first member is inserted into the natural femur to a predetermined depth and means releasably and movably associated therewith for permanent insertion within the natural femur for aligning the distal end of the femoral stem at a desired position within the natural femur.

The first member preferably includes a bore therethrough. The aligning means preferably includes a rod member for slidable insertion through the bore and a second member releasably connected to a distal end of the rod member for permanent insertion into the natural femur for aligning the distal end of the femoral stem at the desired position. The second member includes means for plugging the femoral canal.

The assuring means may be a flange-like portion configured to rest on a cut surface of the natural femur to limit the depth to which the first member can be inserted into the natural femur.

BRIEF DESCRIPTION OF THE DRAWINGS

The present invention can be understood better by reference to the drawings in which.

DETAILED DESCRIPTION OF THE PREFERRED EMBODIMENT

The femoral stem distal centralizer and plug of the present invention are illustrated in FIGS. 1-6. The device 10, shown in FIGS. 1-3, includes a first member, or trial, 12, a rod 14 and a second member, or centralizer 16. A plug 36 extends distally from the centralizer 16.

Figure 1:
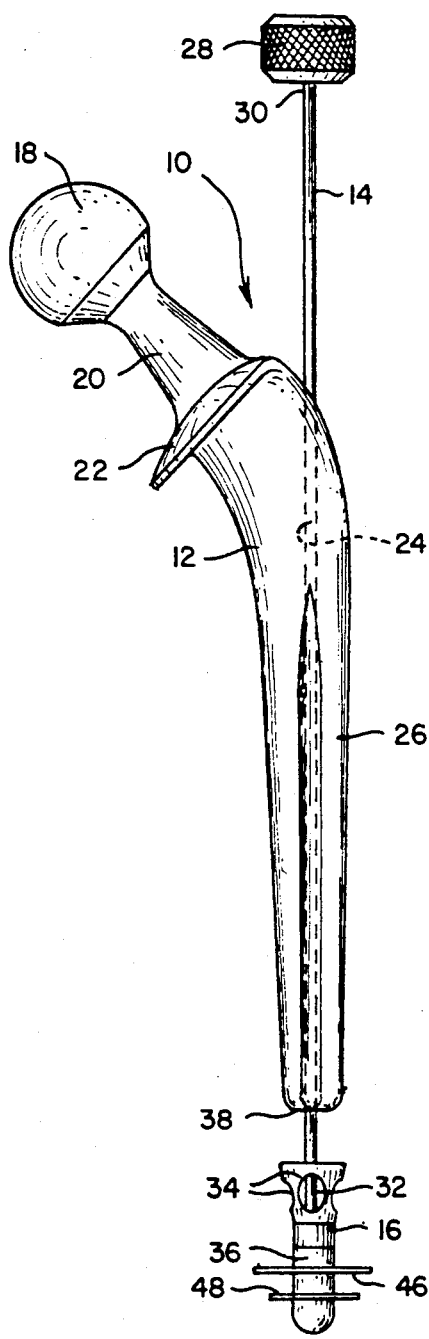
FIG. 1 is a side view of the preferred embodiment of the centralizing and plugging device of the present invention.
Figure 2:
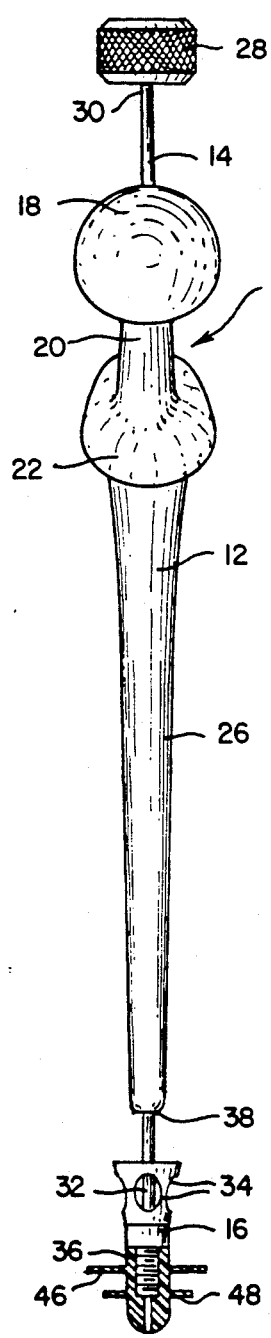
FIG. 2 is a front view of the device of FIG. 1.
Figure 3:
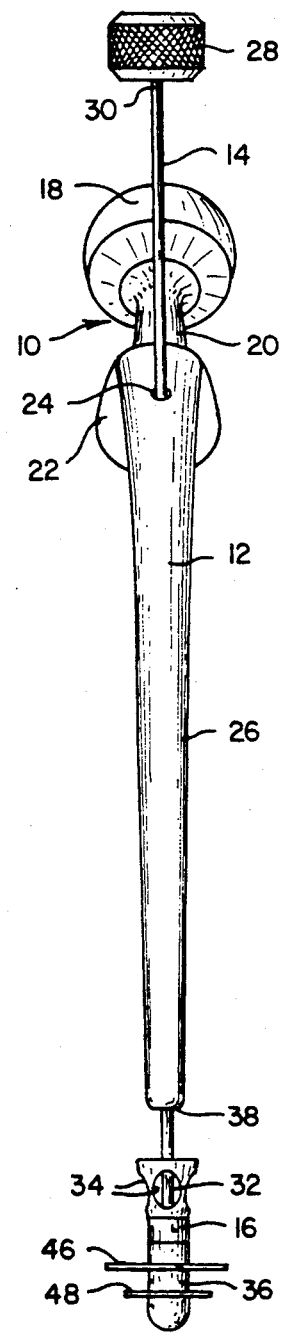
FIG. 3 is a rear view of the device of FIG. 1.
Figure 4:
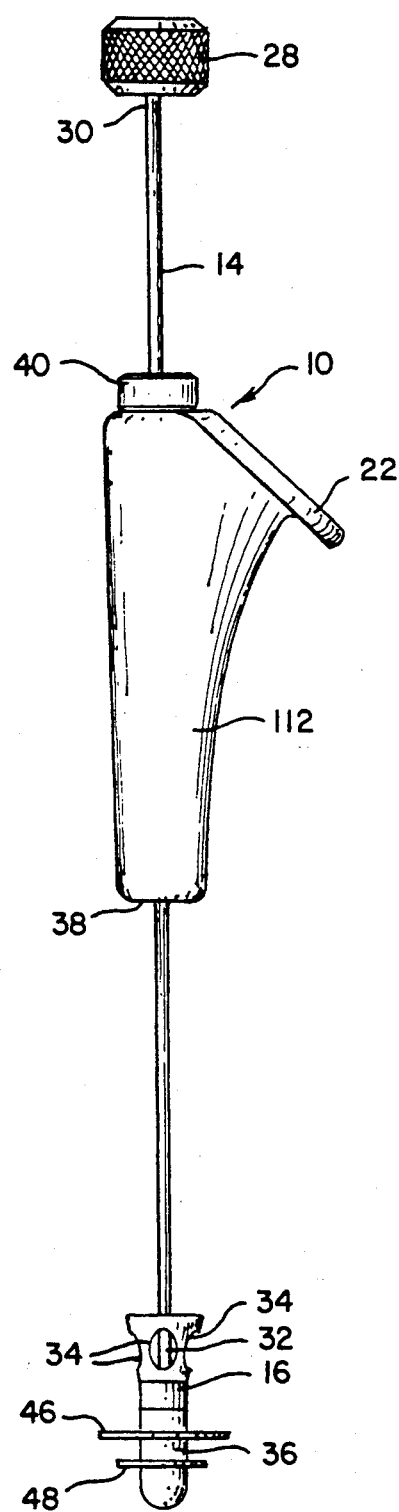
FIG. 4 is a view of an alternative embodiment of the centralizing device of the present invention.

The trial 12, as shown in FIGS. 1-3, is preferably shaped generally like the prosthetic femoral stem (not shown) which will ultimately be placed into the prepared natural femur. As used herein, the term "prepared natural femur" shall mean a femur which has been resected and reamed to accept a prosthetic femoral stem. The natural femoral head and neck typically will have been removed. The device 10 of the present invention can be used to centralize any suitable known prosthetic femoral stem when the canal is reamed to the appropriate size. Although preferred shapes are shown in the Figures, those skilled in the art will recognize that variations in the shape of the device 10 or the prosthetic femoral stem may be made without departing from the intent and scope of the present invention. For example, as shown in FIG. 4, the first member 112 can be any suitable shape capable of temporary insertion into the femoral canal to act as a guide for positioning the centralizer 16 and plug 36.

Referring to FIGS. 1-3, the trial 12 includes a head portion 18, a neck 20, a flange-like member or collar 22 and a generally longitudinal bore 24 extending through the stem or body portion 26 of the trial 12.

Figure 6:
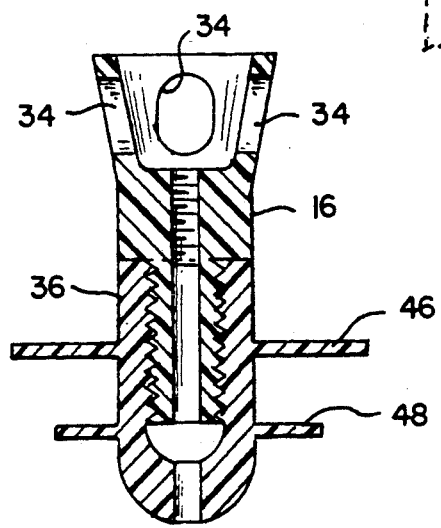
FIG. 6 is a detailed view of the centralizer and plus of the devices shown in FIGS. 1-5.

Rod 14 slides through bore 24 of trial 12. Knob 28, preferably having a knurled surface, is positioned at the proximal end 30 of rod 14. Centralizer 16 is threadably engaged to the distal end 32 of rod 14. Plug 36, as shown in FIG. 6, is preferably threadably connected to centralizer 16. However, any suitable means of connection will suffice.

Centralizer 16 is generally cup shaped or funnel shaped and includes a plurality (three are shown) of openings 34 on the sides of the cupped portion. The openings 34 in the funnel-shaped centralizer 16 allow cement to flow downward against the plug 36 to assure an even envelope. Plug 36 includes upper and lower flexible flanges 46 and 48 which are proportioned to hug the canal. Centralizer 16 and plug 36 are made of biocompatible materials, preferably polymethylmethacrylate or ultra high molecular weight polyethylene.

In use, the device 10 is assembled by sliding rod 14 into bore 24 of trial 12. Centralizer 16 and plug 36 are then threaded onto the distal end 32 of rod 14. After the natural femur is prepared, the assembled device 10 is inserted into the femoral canal. The centralizer 16 and plug 36 are pulled against the distal tip 38 of the body portion 26 of trial 12 during insertion.

Collar 22 rests on a surface of the osteotomized natural femur at the opening to the femoral canal to prevent the trial 12 from entering too deeply within the canal. Collar 22 assures that trial 12 will be inserted within the natural femur to the correct depth. The correct depth may vary from patient to patient and would typically be determined in advance. Device 10 may come in a variety of sizes to accommodate different patients and different needs. Collar 22 also helps to assure that trial 12 is centralized in either the natural or values position whichever is preferred, within the natural femur.

Following insertion of trial 12 into the femoral canal, rod 14 is turned by means of knob 28 to unthread, and thereby release, centralizer 16 and plug 36. The trial 12 and rod 14 are then removed from the femoral canal.

Bone cement can then be inserted into the femoral canal. The bone cement is pressurized or compacted with any suitable known device to remove air pockets. As discussed above, the openings 34 permit the bone cement to flow through and surround the centralizer 16. Plug 36 prevents the cement from moving distally. The prosthetic femoral stem is then inserted into the natural femoral canal.

The cupped portion of centralizer 16 receives the distal end of the femoral stem to assure that it is inserted at the desired depth and centralized. The femoral stem cannot rest against one side or the other of the femoral canal. With the centralizer 16 and plug 36 in place, the femoral stem will rest firmly in a central position within the femoral canal at the desired depth.

Figure 5:
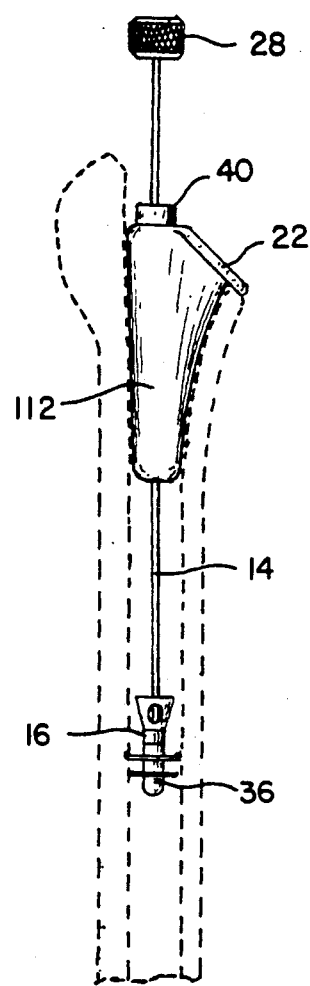
FIG. 5 is a view of the device of FIG. 4 in place in a prepared natural femur.

Referring to FIGS. 4 and 5, an alternative embodiment of the device 10 is shown. The first member 112 is not shaped like the prosthetic femoral stem, but, like the trial 12, acts as a guide for the rod 14 and second member, centralizer 16 and plug 36. A stop 40 is provided on rod 14 to control the depth of placement of centralizer 16 and plug 36 by controlling the depth to which rod 14 can be inserted into the first member 112.

What is claimed is:

1. A device for centralizing a prosthetic femoral stem within a prepared natural femur wherein said femoral stem has a proximal end and a distal end, said device comprising:
   a first member for temporary insertion within said natural femur;
   said first member having limiting means for assuring that said first member is inserted into said natural femur to a predetermined depth; and
   aligning means releasably and movably associated with said first member for permanent insertion within said natural femur and configured for aligning said distal end of said formal stem at a desired position within said natural femur, said aligning means having a cupped portion having a closed distal end, a plurality of openings formed in at least a proximal portion to permit bone cement inserted in use into said natural femur to flow through said openings and surround said cupped portion.

2. The device recited in claim 1 wherein said assuring means is a flange-like portion configured to rest on a cut surface of said natural femur to limit the depth to which said first member can be inserted into said natural femur.

3. The device recited in claim 1 wherein said first member has a bore therethrough for slidably receiving said aligning means.

4. The device recited in claim 3 wherein said aligning means further comprises:
   a rod member for slidable insertion through said bore, said rod member having a proximal end and a distal end; and
   said cupped portion being releasably connected to said distal end of said rod member.

5. The device recited in claim 1 further comprising means releasably connected to said distal end of said cupped portion for plugging the canal of the prepared natural femur to prevent bone cement inserted into said natural femur from moving distally within said natural femur past said plugging means.

6. The device recited in claim 1 further comprising means for controlling the depth to which said aligning means is inserted into the natural femur.

7. A device for centralizing a prosthetic femoral stem within a prepared natural femur wherein said prosthetic femoral stem has a proximal end and a distal end, said device comprising:
   a first member having a shape generally similar to the shape of said prosthetic femoral stem;
   said first member having a bore therethrough;
   a rod member for slidable insertion through said bore, said rod member having a proximal end and a distal end; and
   a second member releasably connected to said distal end of said rod member for permanent insertion into said natural femur, said second member having an inner portion configured for aligning said distal end of said prosthetic femoral stem at a desired portion and including a plurality of openings formed sufficient size therein to permit bone cement inserted in use into said natural femur to flow through said openings and surround said second member.

8. The device recited in claim 7 wherein said device further comprises means positioned distally relative to said second member for plugging the canal of the prepared natural femur to prevent bone cement inserted in use into said natural femur from flowing distally past said second member.

9. The device recited in claim 7 further comprising means for assuring that said first member is inserted into said natural femur to a predetermined depth.

* * * * *